United States Patent [19]

Stammann et al.

[11] Patent Number: 4,593,116
[45] Date of Patent: Jun. 3, 1986

[54] PROCESS FOR THE PRODUCTION OF URETHANES

[75] Inventors: Günter Stammann, Cologne; Johann Grolig, Leverkusen; Robert Becker, Leverkusen; Helmut Waldmann, Leverkusen, all of Fed. Rep. of Germany

[73] Assignee: Bayer Aktiengesellschaft, Leverkusen, Fed. Rep. of Germany

[21] Appl. No.: 620,207

[22] Filed: Jun. 13, 1984

[30] Foreign Application Priority Data

Jun. 23, 1983 [DE] Fed. Rep. of Germany ....... 3322668

[51] Int. Cl.$^4$ .............. C07C 125/065; C07C 125/073; C07C 125/067; C07C 125/075
[52] U.S. Cl. ........................ 560/24; 560/25; 560/27; 560/28; 560/30; 560/32; 560/9; 560/13; 560/115; 560/157; 560/158; 560/162; 560/163; 544/37
[58] Field of Search ............... 560/24, 25, 27, 28, 560/30, 32, 9, 13, 115, 157, 158, 162, 163; 544/37

[56] References Cited

U.S. PATENT DOCUMENTS 4,219,661  8/1980  Becker et al. ................... 560/24
4,262,130  4/1981  Becker et al. ................... 560/24
4,339,592  7/1982  Becker et al. ................. 560/24 X

FOREIGN PATENT DOCUMENTS 105211    4/1974  Fed. Rep. of Germany .
54-115343 7/1979  Japan .
55-7227   1/1980  Japan ................................. 560/24

OTHER PUBLICATIONS

Onoda et al, Chem. Abs., vol. 93 (1980) 167,981c.
Asahi, Chem. Abs., vol. 98 (1983) 178,991k.
Patent Abstracts of Japan, Band 3, Nr. 138, Nov. 16, 1979.

*Primary Examiner*—Bernard Helfin
*Attorney, Agent, or Firm*—Gene Harsh; Joseph C. Gil; Lyndanne M. Whalen

[57] ABSTRACT

Urethanes are made by reacting an organic nitro compound with an organic compound containing at least one hydroxyl group in the presence of carbon monoxide, hydrogen and a catalyst system. The carbon monoxide and hydrogen are used in quantities such that the molar ratio of CO to $H_2$ is from 0.3:1 to 3:1. The catalyst system is made up of at least one noble metal or compound of a noble metal from Group VIIIB of the Periodic System of Elements, at least one organic nitrogen base and a co-catalyst combination of iron or copper oxidic or hydroxidic compound and a chloride compound. The product urethanes are useful in the production of isocyanates and pesticides.

15 Claims, No Drawings

PROCESS FOR THE PRODUCTION OF URETHANES

BACKGROUND OF THE INVENTION

This invention relates to an improved process for the production of urethanes (carbamic acid esters). More specifically, organic nitro compounds and organic compounds containing at least one hydroxy group are reacted in a hydrocarbonylation reaction with a reaction gas containing both carbon monoxide and also hydrogen in a high concentration in the presence of noble metals of the Eighth Secondary Group of the Periodic System and certain co-catalysts to form urethanes.

The production of urethanes from organic nitro compounds, organic hydroxyl compounds and carbon monoxide in the presence of noble metal catalysts is already known. German Offenlegungsschriften Nos. 28 19 826 and 29 03 950, for example, describe processes by which urethanes can be produced in very good volume/time yields through the use of special co-catalysts, such as iron oxychloride or combinations of iron oxides or iron oxide hydrates with activating chlorides, in addition to tertiary amines. Although the urethane synthesis described in these publications affords the possibility of phosgene-free isocyanate production by thermal splitting of the urethanes, not one of those processes has been adopted for industrial scale production. One reason for this non-use on a commercial scale could be that the cost of carrying out these processes is too high to be commercially practical.

Japanese Patent Application No. 53/79076 filed June 29, 1978 and published under the number 55-7227 (1980) discloses that the formation of urethanes from the above-mentioned starting materials in the presence of palladium catalysts is accelerated by the presence of small quantities of hydrogen. This disclosure also emphasizes that the yield of urethane decreases if there is more than 6% volume of hydrogen in the reaction gas. Further, from the Examples of this Japanese publication it appears that the process disclosed therein is based on the use of selenium as the main catalyst component. In the process of the present invention described in more detail hereinafter however, the reaction is carried out in the absence of selenium and hydrogen is present in considerable quantities and enters stoichiometrically into the urethane-forming reaction. Japanese No. 55-7227 also does not use the co-catalysts required in the process of the present invention.

Japanese Patent Application No. 56-68249 filed May 8, 1981 and published under the number 57-185253 in 1982 describes the use of mixtures of carbon monoxide and hydrogen in the synthesis of urethanes from aromatic nitro compounds in the presence of amino compounds which correspond to the nitro compounds and which are simultaneously reacted to form urethanes. In this disclosed process, (which does not employ the co-catalysts required in the present invention), uneconomically large quantities of noble metal catalysts must be used, as is evident from the general description and the Examples given therein.

SUMMARY OF THE INVENTION

It is an object of the present invention to provide an economic process for the production of urethanes.

It is also an object of the present invention to provide a process for the production of urethanes in which a mixture of carbon monoxide and hydrogen rather than pure carbon monoxide is employed.

These and other objects which will be apparent to those skilled in the art are accomplished by reacting an organic nitro compound with an organic compound containing at least one hydroxy group in the presence of a catalyst system, carbon monoxide and hydrogen. The molar ratio of carbon monoxide to hydrogen is from 0.3:1 to 3:1. The catalyst system is made up of (a) at least one noble metal or compound of a noble metal of Group VIIIB of the Periodic System of Elements and (b) at least one organic nitrogen base and (c) at least one co-catalyst. The co-catalyst is a combination of (1) at least one oxidic or hydroxidic compound of iron and/or copper and (2) at least one compound containing chlorine anionically bound as chloride. The compound containing anionically bound chlorine may be a chloride and/or oxychloride of elements of Groups IIA, IVA, VA, and/or I through VIIIB of the Periodic System of Elements other than the noble metals of Group VIIIB and/or an organic ammonium chloride.

DETAILED DESCRIPTION OF THE INVENTION

The present invention relates to a process for the production of urethanes by reacting organic nitro compounds with organic compounds containing at least one hydroxy group and carbon monoxide in the presence of a catalyst system. The catalyst system contains at least one noble metal or noble metal compound from the Eighth Secondary Group of the Periodic System of Elements, at least one organic nitrogen base and at least one co-catalyst. The co-catalyst is a combination of at least one oxide or hydroxide of iron or copper and at least one compound containing chlorine anionically bound as chloride selected from chlorides or oxychlorides of elements of the Third to Fifth Main Group and/or of the First to Eighth Secondary Group of the Periodic System, except for noble metals of the Eighth Secondary Group, and organic ammonium chlorides. The carbon monoxide is used together with hydrogen in a molar ratio of $CO:H_2$ of from 0.3:1 to 1.

In conventional processes for producing urethanes from nitro compounds, organic hydroxy compounds and carbon monoxide, the nitro compounds are reduced and carbonylated with a total consumption of 3 molecules of carbon monoxide for each nitro group, as can be seen from equation (1) below:

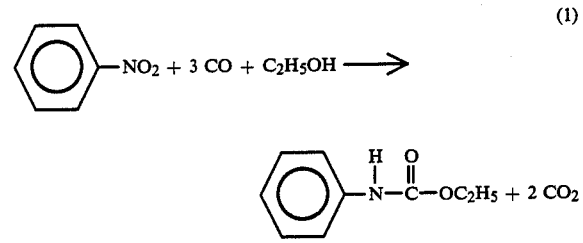

The reaction on which the process of the present invention is essentially based is the hydrocarbonylation reaction which takes place in accordance with equation (2) and in which only one molecule of carbon monoxide is consumed for each nitro group to be reacted:

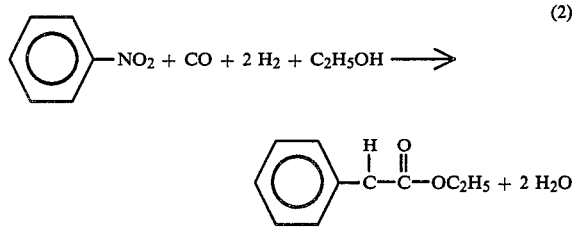

$$\text{PhNO}_2 + CO + 2H_2 + C_2H_5OH \longrightarrow \text{Ph-CH(OH)-C(O)-OC}_2H_5 + 2H_2O \quad (2)$$

The less economical carbonylation reaction which takes place in accordance with equation (1) (using up 3 molecules of carbon monoxide for each nitro group) also takes place in the process of the present invention to a certain extent, depending upon the reaction conditions. The overall reaction which takes place in the process of/the present invention may be represented by the stoichiometry expressed in equation (3) with reference, by way of example, to phenyl urethane:

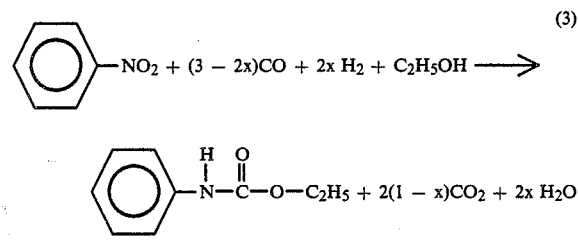

$$\text{PhNO}_2 + (3-2x)CO + 2xH_2 + C_2H_5OH \longrightarrow \text{Ph-NH-C(O)-O-C}_2H_5 + 2(1-x)CO_2 + 2xH_2O \quad (3)$$

Equations (1) and (2) and also equation (3) derived therefrom are not intended to explain the theoretical course of the reaction in any way. Rather, these equations summarize the starting materials used and also the main products of the process of the present invention with specific reference to the production of N-phenyl-O-ethyl urethane.

The principal advantage of the process of the present invention lies in the fact that, instead of carbon monoxide, mixtures of carbon monoxide and hydrogen may be used as the reaction gas. In general, mixtures of carbon monoxide and hydrogen are less expensive than pure carbon monoxide if CO and $H_2$ are counted as equivalent reduction equivalents. It is clear that a process which uses mixtures of carbon monoxide and hydrogen as the starting gas is more cost-effective than a process using pure carbon monoxide which first has to be separated off from a mixture of carbon monoxide and hydrogen (e.g., by low-temperature separation or by the cosorb process). In fact, a considerable amount of the production cost of carbon monoxide from a reforming process is attributable to the energy and equipment required to separate carbon monoxide and hydrogen.

A major advantage of the process of the present invention lies in the chemical utilization of the hydrogen present in the starting gas for urethane formation. According to equation (1), 2 molecules of carbon monoxide are lost as $CO_2$ due to reduction of the nitro group and 1 molecule of carbon monoxide is incorporated in the urethane molecule. In the process represented by equation (2), however, reduction of the nitro group is brought about by using 2 molecules of hydrogen and 1 molecule of carbon monoxide to synthesize the urethane group. It is surprising that urethane formation proceeds largely in accordance with equation (2) because water is formed in stoichiometric quantities. It would have been expected that the urethanes formed would be hydrolytically destroyed under the reaction conditions in the presence of the water of reaction.

Suitable starting compounds for the process of the present invention are any organic nitro compounds, (i.e., any organic compounds containing nitro groups) that are otherwise inert under the conditions of the process of the present invention, containing at least one aliphatically, cycloaliphatically and/or aromatically bound nitro group and having a molecular weight of generally from 61 to 400 (preferably from 123 to 286) and any organic compounds containing at least one hydroxy group. Examples of such hydroxy group-containing materials are substituted or unsubstituted aliphatic, cycloaliphatic and/or aromatic mono-, di- or polyhydroxy compounds having a molecular weight of generally from 32 to 228 and preferably from 32 to 102.

Examples of suitable aromatic nitro compounds include: nitrobenzene, o-dinitrobenzene, m-dinitrobenzene, p-dinitrobenzene, o-chloronitrobenzene, m-chloronitrobenzene, o-nitrotoluene, m-nitrotoluene, p-nitrotoluene, 2,3-dinitrotoluene, 2,4-dinitrotoluene, 2,5-dinitrotoluene, 2,6-dinitrotoluene, 3,4-dinitrotoluene, 3-nitro-o-xylene, 4-nitro-o-xylene, 2-nitro-m-xylene, 4-nitro-m-xylene, 5-nitro-m-xylene, nitro-p-xylene, 3,4-dinitro-o-xylene, 3,5-dinitro-o-xylene, 3,6-dinitro-o-xylene, 4,8-dinitro-o-xylene, 2,4-dinitro-m-xylene, 2,5-dinitro-m-xylene, 4,5-dinitro-m-xylene, 4,6-dinitro-m-xylene, 2,3-dinitro-p-xylene, 2,6-dinitro-p-xylene, 1-nitronaphthalene, 2-nitronapthalene, dinitronaphthalenes, nitroanthracenes, nitrodiphenyls, bis-(nitrophenyl)-methanes, bis-(nitrophenyl)-thioethers, bis-(nitrophenyl)-sulfones, nitrodiphenoxyalkanes, nitrophenothiazines.

Cycloaliphatic nitro compounds which may be used in accordance with the present invention include nitrocyclobutane, nitrocyclopentane, nitrocyclohexane, 1,2-dinitrocyclohexane, 1,3-dinitrocyclohexane, 1,4-dinitrocyclohexane and bis-(nitrocyclohexyl)-methanes.

Examples of appropriate nitroalkanes include nitromethane, nitroethane, 1-nitropropane, 2-nitropropane, nitrobutanes, nitropentanes, nitrohexanes, nitrodecanes, nitrocetanes, 1,2-dinitroethane, 1,2-dinitropropane, 1,3-dinitropropane, dinitrobutanes, dinitropentanes, dinitrohexanes, dinitrodecanes, phenyl nitromethane, bis-(nitromethyl)-cyclohexanes, bis-(nitromethyl)-benzenes and ω-nitrocarboxylic acid nitriles.

Preferred nitro compounds for the process of the present invention are aromatic nitro compounds such as, nitrobenzene, 1,3-dinitrobenzene, 2,4-dinitrotoluene, 2,6-dinitrotoluene, dinitronapthalenes such as 1,5-dinitronaphthalene and 2,4'- and 4,4'-dinitrodiphenylmethane. Other particularly preferred nitro compounds for the process of the present invention are binuclear aromatic dinitro compounds from the diphenyl methane series of the type described as intermediate products for diisocyanates in European Patent No. 24,665. It is especially preferred to use nitrobenzene and technical isomer mixtures of dinitrotoluene which contain 2,4-dinitrotoluene as their principal constituent.

Organic compounds containing hydroxy groups suitable for use in accordance with the present invention include monohydric alcohols, polyhydric alcohols, monohydric phenols and polyhydric phenols. Alcohols are preferred to phenols.

Suitable alcohols include linear or branched alkanols, cycloalkanols, alkenols, cycloalkenols, aralkyl alcohols and the like, in each case mono-functional or poly-functional. These alcohols may contain a substituent having an oxygen, nitrogen, sulfur or a halogen atom, for example a halogen, sulfoxide, sulfone, amine, amide, carbonyl or carboxylic acid ester group. The following are examples of appropriate monohydric alcohols: methyl alcohol, ethyl alcohol, propanol, isopropanol, butanol, pentanol, hexanol, cyclohexanol and benzyl alcohol. Suitable polyhydric alcohols are, for example, ethylene glycol, propylene glycol, dipropylene glycol, glycerol, hexane triol and the like and also higher polyols. Monohydric aliphatic alcohols containing from 1 to 6 carbon atoms are preferred and ethyl alcohol is most preferred.

Phenols suitable for use in the practice of the present invention include phenol, chlorophenols, cresols, ethylphenols, propylphenols, butylphenols and higher alkyl phenols, pyrocatechol, resorcinol, 4,4'-dihydroxydiphenylmethane, bisphenol-A, anthranol, phenanthrol, pyrogallol or phloroglucinol.

In carrying out the process of the present invention, the organic hydroxy compounds are generally used in quantities such that when mononitro compounds are used as the starting material, the equivalent ratio between nitro groups and hydroxyl groups is in the range from 1:0.5 to 1:100 and preferably in the range from 1:1 to 1:100. If a dinitro compound is used as the starting material, the equivalent ratio between nitro groups and hydroxyl groups should be in the range from 1:1 to 1:100.

It is particularly preferred to use the alcohols described above as preferred in excess because the unreacted excess serves as reaction medium.

In addition to the essential noble metal component, the catalyst systems used in the process according to the invention contain a first co-catalyst component, which contains a metal compound capable of redox reactions and a second co-catalyst component in the form of an organic amine.

The noble metal catalyst may be a free noble metal of the 8th secondary group of the Periodic System of Elements or a compound of those metals which is soluble in the reaction medium. For example, the noble metal may be used in finely divided, metallic form on inert supports such as active carbon, aluminum oxide, quartz, insoluble silicates, barium sulfate, molybdenum oxide, tungsten oxide or insoluble spinel-like compounds. The noble metals are more advantageously added in the form of compounds which are soluble in the reaction medium, for example in the form of chlorides, bromides, iodides, chloro complexes, bromo complexes, iodo complexes, acetates, acetyl acetonates and other soluble noble metal compounds. However, it is possible to use noble metal compounds which are poorly soluble such as oxides, because solubility-promoting co-catalyst components (for example activating chlorides) are also used in the catalyst system.

Suitable noble metal components are Ru, Rh, Pd, Os and Pt. Preferred noble metals are Ru, Rh and Pd. It is particularly preferred to use palladium and ruthenium, particularly in the form of their soluble chlorides.

The preferred concentration of the noble metal catalyst component, based on the reaction mixture, including any solvent used, generally amounts to between 0.0001 and 0.1 wt. % and, more particularly, to between 0.005 and 0.05 wt. %, expressed as noble metal. At lower noble metal concentrations, the velocity of the reaction is too low. Although higher noble metal concentrations are possible, they are uneconomical because they do not produce any further increase in the yield of urethane.

The co-catalyst component is a combination of at least one oxidic or hydroxidic compound of iron or copper and at least one compound containing chlorine anionically bound as chloride. Examples of such chlorine-containing compounds are chlorides or oxychlorides of elements of the Third to Fifth Main Groups and/or the First to Eighth Secondary Groups of the Periodic System of Elements (except for noble metals of the Eighth Secondary Group) and organic ammonium chlorides.

Suitable oxidic and hydroxidic co-catalyst components are, for example, FeO, $\alpha$-Fe$_2$O$_3$, $\gamma$-Fe$_2$O$_3$, $\alpha$-FeO(OH), $\beta$-FeO(OH), Fe(OH)$_2$, Fe(OH)$_3$, Cu$_2$O, CuO, Cu$_2$O(OH)$_2$, Cu(OH)$_2$ and Cu$_2$(OH)$_2$CO$_3$, as well as other oxides, hydroxides, oxide hydrates or hydroxy carbonates (basic carbonates) of iron or copper. Preferred co-catalyst components are those compounds identified above by formulae with $\alpha$- and $\gamma$-Fe$_2$O$_3$ being particularly preferred.

The chlorine-containing co-catalyst components may be compounds of elements of the Third to Fifth Main Groups and/or of the First to Eighth Secondary Groups of the Periodic System of Elements, except for noble metals of the Eight Secondary Group containing chlorine anionically bound as chloride which preferably are at least partly soluble in the reaction mixture (optionally with hydrolysis or alcoholysis) or organic ammonium chlorides. Suitable metal chloride compounds are, for example, AlCl$_3$, TiOCl$_2$, VCl$_3$, VCl$_5$, VOCl$_3$, CrCl$_3$, MnCl$_2$, MnOCl, FeCl$_2$, FeOCl, FeCl$_3$, CoCl$_2$, NiCl$_2$, Cu$_2$Cl$_2$, CuCl$_2$, Cu$_2$OCl$_2$, ZnCl$_2$, NbCl$_5$, MoCl$_6$, WCl$_6$. The metal chlorides mentioned by way of example may of course also be used in the form of complex salts, for example in the form of the corresponding chloride hydrates or complexes with amine bases. Suitable organic ammonium chlorides are, for example, tetramethyl ammonium chloride, tetraethyl ammonium chloride, tetrabutyl ammonium chloride, any quaternary ammonium chlorides which contain different alkyl radicals on the nitrogen, (e.g., methyl tributyl ammonium chloride) and in particular hydrochlorides of the amine base used as a catalyst. It is of course also possible to use as an organic ammonium chloride any compounds which react off in situ to form ammonium chlorides of the type described above. For example, it is possible to use carbamic acid chlorides of the type obtained by the addition of HCl to isocyanates, because carbamic acid chlorides such as these are hydrolytically converted into the corresponding ammonium chlorides. Preferred metal chloride co-catalyst components are MnCl$_2$, FeCl$_2$, FeCl$_3$ and CuCl$_2$, their hydrates and amine complexes. Iron chlorides, their hydrates and amine complexes are particularly preferred. Preferred organic ammonium chloride catalyst components are the hydrochlorides of the amines used as co-catalyst. It is of course also possible to use any combinations of the chloride compounds mentioned above. Instead of using the above-mentioned combinations of the oxides and/or hydroxides of iron and copper and compounds containing anionically bonded chlorine, it is of course also possible to use compounds which represent a stoichiometric combination of individual compounds such as these. Thus, for example, the compound Cu$_2$(OH)$_2$Cl$_2$ or other atacamites may be used instead of the combination of copper(II)hydroxide and copper(II)chloride.

Correspondingly, it would also be possible to use γ- and β-Fe$_2$(OH)$_3$Cl.

In the co-catalyst combination, the individual components are present in quantitative ratios such that, for every metal atom present there are from 0.1 to 2 and preferably from 0.5 to 1.5 chlorine atoms. The percentage by weight of oxidic or hydroxidic compound of iron and/or copper co-catalyst component should preferably make up at least one-third and at most nine-tenths of the total co-catalyst component.

The co-catalyst components are generally used in total quantities of from 0.5 to 20 wt. % (preferably in total quantities of from 2 to 10 wt. %) based on the total quantity of reaction mixture, including any solvent used.

The presence of the co-catalyst combination is essential to achieve a high order of the urethane-forming reaction according to equation (2). That is, the presence of the co-catalyst component ensures that a high percentage of the hydrogen present in the gas phase will take part in the hydrocarbonylation reaction of the nitro compound. By virtue of the low chloride content of the co-catalyst component, the process of the present invention may be carried out without any serious corrosion problems.

Suitable organic nitrogen bases include tertiary organic amines and/or primary or secondary amines structurally related to the nitro compounds and organic hydroxyl compounds used as starting materials.

Suitable tertiary amines are aliphatic, cycloaliphatic, aromatic, araliphatic or heterocyclic tertiary amines having a molecular weight in the range of from 59 to about 10,000 and preferably in the range of from 59 to 300. Tertiary amines containing substituents which are inert under the reaction conditions, such as halogen, cyano, alkoxy, phenoxy, thiophenoxy, carbonyl, carboalkoxy and/or thiocarbonyl substituents, are also suitable. Specific examples of suitable tertiary amines are trimethylamine; triethylamine; tripropylamine, tributylamine; cycloaliphatic tertiary amines, such as N,N-dimethyl cyclohexylamine, N,N-diethyl cyclohexylamine, 1,4-diaza[2,2,2]-bicyclooctane; aromatic tertiary amines, such as N,N-dimethyl aniline, N,N-dimethyl-4-toluidine, N,N-diethylaniline; and also heteroaromatic tertiary amines, such as pyridine, the picolines, quinoline, isoquinoline, quinaldine, lepidine, imidazole, pyrazole, benzimidazole, pyrolyzed polyacrylonitrile and polyvinyl pyridine. These amines may be used in the process of the present invention in quantities of from 0.5 to about 5 wt. %, based in each case on the total quantity of non-gaseous starting materials.

However, preferred organic nitrogen bases are primary or secondary amines which are structurally related to the nitro compounds and organic hydroxy compounds used as starting materials. For example, if an organic nitro compound of the formula R$^1$—NO$_2$ is used in the present invention as a starting material, a structurally related primary or secondary amine may be derived therefrom by reduction of the nitro group to the amine group or by N-alkylation of the amine group by the alcohol R$^2$—OH used as starting material. Such structurally related primary or secondary amines may be represented by the formula

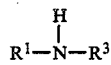

in which
R$^1$=R$^1$ from R$^1$ from R$^1$—NO$_2$ and R$^3$=H or R$^2$ from R$^2$—OH.

If the nitro compound used as a starting material contains more than one nitro group, amines which contain the structural features of amines of the type represented by the above-given formula, are formally derived therefrom. In that case, however, any nitro groups present in the amine compound react off in accordance with the present invention to form the corresponding urethanes.

The primary or secondary amines which are structurally related to the starting materials may be present in the process of the present invention in quantities of up to about 15 wt. %, based on the starting mixture as a whole (including solvent). These amines are preferably used in a quantity which, in molar terms, makes up from one-twentieth to one-third of the nitro compound used. In this connection, however, it is important to point out that any primary amines used, even if employed in relatively large quantities, act solely as a catalyst because, in contrast to the teaching of the above-cited Japanese Publication No. 57-185253, these amines do not react to form urethanes in the sense of a starting material.

The catalyst system used in the process of the present invention may be supplemented by additions of finely divided metallic iron or nickel. These metal additions accelerate the reaction. Where chloride-containing co-catalysts are present, an addition of iron also has a corrosion-inhibiting effect. In general, up to about 3 wt. % (based on the total reaction mixture including any solvent used), of metallic iron or nickel may be added.

In addition to the special catalyst system, it is essential to the invention to use a mixture of carbon monoxide and hydrogen instead of pure carbon monoxide. Suitable starting gases contain carbon monoxide and hydrogen in a molar ratio or ratio by volume of from 0.3:1 to 3:1 and preferably in a molar ratio or ratio by volume of from 0.5:1 to 1.5:1. In addition to the main components, carbon monoxide and hydrogen, the starting gas—depending on its origin—may contain other constituents such as helium, argon, nitrogen, methane and/or carbon dioxide which show substantially inert behavior under the reaction conditions of the process and which do not affect the reaction.

The starting gas for the process of the present invention may be produced in any way known to those in the art including for example, mixing the individual components CO and H$_2$. However, the economic advantages of the process of the present invention are best realized when carried out with a suitable gas supply or gas production system in which the CO/H$_2$-ratio is from 0.3:1 to 3:1. Such gas supply is preferably free from sulfur, optionally after a purification step. Since synthesis gases made up of carbon monoxide and hydrogen may be used in the present invention in the same composition in which they are formed and accumulated in conventional processes for the production of synthesis gas, the process of the present invention makes it possible (in an integrated gas and urethane production plant) to use a smaller gas production unit than would be possible in conventional processes using only carbon monoxide. Larger gas production units are necessary in conventional processes because those processes use approximately 3 times more carbon monoxide than the present invention thereby requiring a correspondingly larger gas production unit. Additionally, the hydrogen accumulating during the conventional process cannot be used.

Suitable gas production processes are used on a wide scale and are described, for example, in "Ullmanns' Enzyklopadie der technischen Chemie", Vol. 14, pages 357 to 474 (Weinheim/New York, 1977) and in Winnacker, Kuchler, "Chemische Technologie", Vol. 5, pages 260–272 and pages 422–450 (Munich/Vienna, 1981) and also in Kirk-Othmer "Encyclopedia of Chemical Technology", Vol. 10, pages 353 to 442 (New York, 1966).

It can be seen from equation (3) that the maximum hydrogen demand of the process of the present invention is achieved with $x = 1$ (i.e., with 2 moles of $H_2$ per mole of CO and per mole of urethane groups produced) which corresponds to a $CO/H_2$-ratio of 1:2 in the starting gas. If the gas supplied from a natural gas reformer, for example, has a higher hydrogen content any of the following measures may be taken:

(1) the required amount of hydrogen may be removed from the hydrogen-rich gas supplied by an inexpensive separation process (for example, the Monsanto membrane separation process or the pressure-swing process) and the hydrogen thus-removed may be put to another use; or (2) the reaction may be carried out in such a way (which is possible with this catalyst system) that, in addition to urethane production, the nitro compound is simultaneously reduced to the corresponding amine which amine may then be used, for example, for the production of dyes; or (3) the hydrogen-rich gas may be used for urethane production and the hydrogen-containing gas passed through used as a heating gas, for example for underfiring reformers.

The lower limit to the quantity of synthesis gas required for the process of the present invention is imposed by the stoichiometry formulated in equation (3) with reference to the example of phenyl urethane. However, it is generally advantageous in the case of "straight flow" operation, to use from 1.05 to 20 times and preferably from 1.05 to 10 times the stoichiometrically necessary quantity.

"Gas recycling" is preferred to "straight flow". To carry out the process with recycle gas, the reaction gas leaving the last reactor is returned via a compressor to the entrance of the reaction vessel, mixed with fresh starting gas and introduced into the reaction vessel. The $CO_2$ formed during urethane production is removed from the recycle gas system via a suitable separation stage. It is desirable that the inert gas constituents in the starting gas with the exception of $CO_2$ should be minimal to prevent the concentration of inert gas in the recycle gas.

The gas recycling procedure affords several advantages. First, the starting gas is optimally utilized because, apart from the minimal losses for the removal of $CO_2$, only the stoichiometric gas demand has to be supplied. Second, the enthalpy of the highly exothermic urethane-forming reaction may be completely or partly dissipated through a condenser in the recycle gas system. (The dissipation of heat via heat exchangers in the solids-containing reaction medium is technically more difficult). And third, the concentration of the gaseous reactants, carbon monoxide and hydrogen, may be adapted to meet the requirements of the reaction kinetics and is largely independent of the concentrations in the starting gas.

The recycle gas system is preferably operated under a pressure similar to the reaction stage. The ratio by volume of the recycle gas to the fresh starting gas is generally in the range from 1:1 to 100:1 and preferably in the range from 1:1 to about 30:1. The removal of the $CO_2$ produced and of any $CO_2$ present in the starting gas from the recycle gas may be carried out by known processes, such as membrane separation processes or absorption processes. Where the $CO_2$ is removed by absorption, it is favorable to use an absorption liquid or a mixture of liquids which are in any case used in the reaction stage of the urethane production process, because this avoids the entrainment of any foreign components. For example, ethanol, nitrobenzene, aniline and N-ethyl aniline or mixtures thereof may be used as absorption liquids for $CO_2$ where N-phenyl-o-ethyl urethane is being produced. Where there is a high $CO_2$ partial pressure in the recycle gas system, the removal of $CO_2$ by condensation is particularly economical and is particularly preferred.

Where $CO_2$ has to be removed from the recycle gas (that is, where x in equation (3) is less than 1), its removal is easier if a high level of $CO_2$ is present than if the $CO_2$ is a minimal residual content approaching 0%. Since $CO_2$ surprisingly does not affect the reaction, even in relatively high concentrations, a concentration of up to 70% by volume (preferably from 20 to 60% by volume) $CO_2$ may be used as the inert gas component of the recycle gas.

The reaction of the present invention may be carried out in the presence or absence of a solvent. In general, the organic hydroxyl compound which is preferably used in excess also acts as solvent. However, it is also possible to use inert solvents which may make up as much as 80 wt. % of the total reaction mixture. The quantity of solvent used, irrespective of whether it is the hydroxyl compound used in excess or an inert solvent, should be such that the heat of reaction of the exothermic urethane-forming reaction may be dissipated without any unacceptable increase in temperature, leaving a stirrable reaction phase in the reactor.

Suitable solvents are those which are inert to the reaction components and to the catalyst system. Such solvents include, for example, aromatic, cycloaliphatic and aliphatic hydrocarbons which may optionally be substituted by halogen. Specific examples of such solvents are benzene, toluene, xylene, chlorobenzene, dichlorobenzene, trichlorobenzene, chloronaphthalene, cyclohexane, methyl cyclohexane, methylene chloride, carbon tetrachloride, tetrachloroethane, trichlorotrifluoroethane and similar compounds.

The reaction temperature is generally in the range from 100° to about 300° C., preferably in the range from 130° to 250° C. and, most preferably, in the range from 140° to 220° C. The pressure under which the reaction is carried out should be such that a liquid phase is always present. Such pressures are generally in the range from 5 to 500 bars, preferably in the range from 30 to 300 bars at the reaction temperature. Depending upon the nitro compound and/or hydroxy compound used, the reaction time required for a quantitative conversion amounts to between a few minutes and several hours.

The production of urethanes in accordance with the present invention may be carried out either continuously or in batches. However, the advantages with respect to material savings by using carbon monoxide/hydrogen mixtures instead of carbon monoxide as the starting gas only become apparent in a continuously operated large-scale installation in conjunction with a suitable gas supply. Therefore, continuous operation of the process is preferred.

The production of urethanes in batches is carried out in a reactor while the continuous production of urethanes is generally carried out in a cascade of from 2 to about 8 (preferably from 3 to 5) reactors designed for the pressures applied in the process of the present invention. Since most of the catalyst systems of the present invention contain insoluble solids or form insoluble solids during the reaction, the solids-containing reaction mixture (suspension) may be vigorously stirred. Instead of stirring, the suspension may also be moved by vigorous pump recirculation in stirrer-equipped vessels comprising a loop or in loop reactors optionally having heat exchangers advantageously arranged in the loop. Where the reaction is carried out continuously, it is also possible to guarantee adequate recirculation of the reaction suspension by injecting the starting materials and the reaction gases, for example in a cascade of jet nozzle reactors.

The liquid starting materials for the process of the present invention, including the liquid amine catalyst components may be delivered to the reaction vessel either individually or in admixture. However, it is of advantage to introduce the soluble catalyst constituents in solution in the liquid starting materials and to introduce any solid catalyst constituents present (for example, $\alpha\text{-}Fe_2O_3$) into the reaction vessel as a suspension in all or part of the starting solution.

A reactor cascade comprising more than two reactors is preferably used for carrying out the process of the present invention because it enables the urethane yield to be optimized by delivering one-third to about two-thirds of the nitro compound starting material to the first reactor and the remainder of the nitro compound to one or more of the following reactors, except for the last, and/or by operating the reactors at graduated temperatures.

The starting gas or the reaction gas may flow in parallel current, in cross current or in countercurrent to the reaction suspension, preferably in parallel current.

Where the urethane-forming catalyst system used also shows high hydrogenation activity or where a high hydrogen partial pressure prevails in the reaction zone, other products can be obtained in addition to the urethane. For example, when the starting materials are nitrobenzene and ethanol, in addition to the product urethane, aniline, N-ethyl aniline, N,N-diethyl aniline, N,N'-diphenyl urea, quinaldine and triphenyl isocyanurate may also be formed. Without defining any particular mode of reaction in this direction, the formation of these secondary products may be described by equations (4) to (9) below:

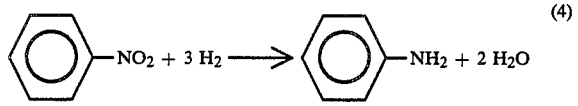 (4)

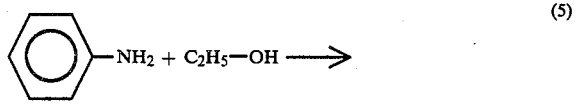 (5)

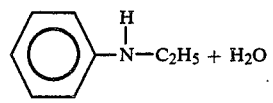

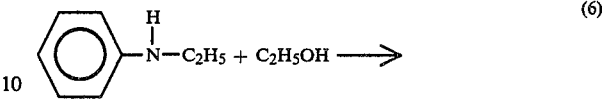 (6)

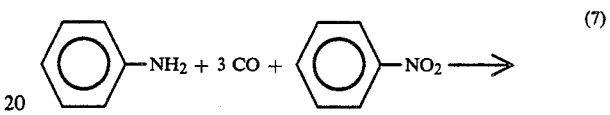 (7)

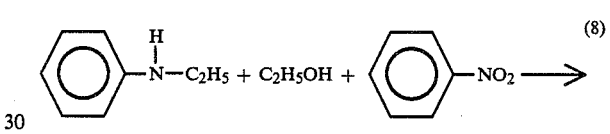 (8)

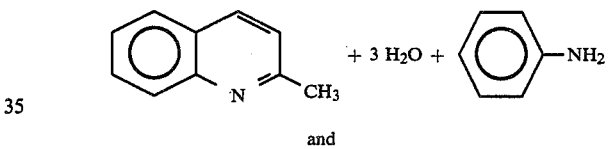 (9)

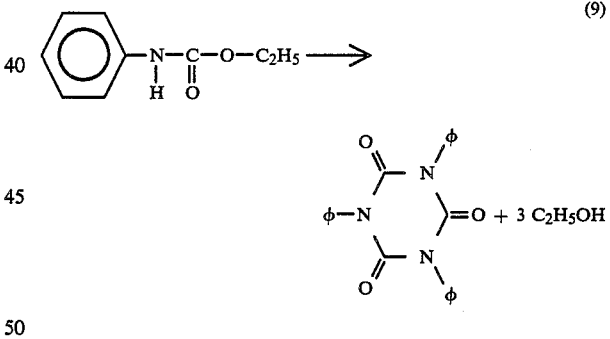

($\phi$ — phenyl group).

The secondary products N,N-diethyl aniline, quinaldine and triphenyl isocyanurate may together make up as much as about 4 mole percent (based on the nitrobenzene used), although they generally make up less than 2 mole % of the reaction product. Since quinaldine and N,N'-diethyl aniline also represent tertiary amines useful in the catalyst systems of the present invention, the quantities of these amines produced may be used to replace lost amine catalyst.

It can readily be seen that the products formed in accordance with equations (4) to (7) represent or are derived from hydrogenation products of the nitro compound (in this case nitrobenzene). If these products occur in excessive, undesirable concentrations, their formation may be suppressed by measures which impair hydrogenation of the nitrobenzene. For example, the hydrogen partial pressure in the reactors may be reduced by adjusting other recycle gas concentrations and/or the nitro compound used may be delivered in partial streams to individual reactors of a cascade of reactors. Even minor changes in the co-catalyst system are sufficient to increase the selectivity of urethane formation, particularly when the concentration of the iron and/or copper oxide or hydroxide co-catalyst component is increased.

On the other hand, it is also generally possible to re-use (i.e. recycle) the secondary products together with the starting materials of the process of the present invention. In general, the concentrations of the secondary products remain substantially constant after repeated recycling, in other words a stationary condition is developed. In this case, the secondary products occur only as constituents of a liquid recycle stream and are no longer secondary products of the process. In other words, these secondary products no longer impair the selectivity of urethane formation. Deviations from the stationary concentrations of the secondary products may be corrected by one of the above-mentioned measures and minor deviations may even be corrected by a purge.

With regard to the reaction itself and, more particularly, with regard to the choice of quantity of nitro compound used, the quantity of solvent and the excess of organic hydroxy compound, it is important to ensure that the concentration of water in the liquid phase after the reaction does not exceed 10 wt. % preferably 7 wt. % (assuming a complete conversion of the nitro compound in accordance with equation (3)). This limit of 10 wt. % water is significant because with higher concentrations of water the velocity and the selectivity of the urethane-forming reaction decrease to a considerable extent. Although the water of reaction can be bound by chemical or physical methods (for example, by the addition of ortho esters, ketals, acetals or molecular sieves (zeolites) in the reaction stage), it is generally uneconomical to do so because working up of the urethane would be made more difficult.

Working up of the reaction mixtures may be carried out by any of a number of techniques known to those skilled in the art. An example of one such technique is described below.

The reaction gas and the liquid product solution, in which solid catalyst constituents are suspended, may be released together from the last reaction stage (for example through a multiphase tubular coil evaporator) and fed into a gas/liquid separator which also acts as a concentrator. The temperature and pressure of this separator are preferably selected in such a way that a gas phase which contains the reaction gases, water and part of the solvent or of the organic hydroxy compound, and a liquid phase which corresponds to the concentrated, solids-containing reaction solution (suspension) are formed. However, it is also possible to separate the reaction gas and the catalyst-containing reaction solution (suspension) by means of a pressure separator under the reaction pressure which would release only the reaction solution.

After the water and the organic constituents have been condensed out, the gas phase may be adjusted to the required $CO_2$-concentration and returned to the reaction after the addition of fresh starting gas.

The suspension containing the catalyst constituents, solvent or organic hydroxy compound and the process products is freed from solid catalyst constituents by filtration, decantation or centrifuging (at around 30° to 80° C.). The catalyst mass or catalyst sludge separated off contains the chloride and copper and/or iron oxide or hydroxide catalyst component and, deposited thereon in finely divided form, the noble metal catalyst component and any precipitated complexes of the amine bases with the metal halides of the catalyst system. The catalyst mass may be returned to the reaction stage, after which the filtrate is further worked up.

Separation of the catalyst mass from the urethane-containing filtrate may be carried out, for example, in suitable filter units, in centrifuges, in decanters or in crossflow filtration apparatus. Crossflow filtration, in which the suspension is thickened in tubular membranes to the consistency of a catalyst sludge which can still just be pumped, is particularly preferred for solid/liquid separation.

The filtrate may contain small quantities of dissolved or colloidal inorganic catalyst constituents. These constituents are best separated off before further working up, for example by an ion exchanger or by precipitation. If, for example, a catalyst system containing iron and chloride ions is used, precipitation of the iron compounds which are still dissolved may be obtained by the addition of very small quantities of an alkali hydroxide (for example sodium hydroxide) or by the addition of an alkali or alkaline earth alcoholate. The precipitated or flocculated iron compound may then be removed in a second stage for solid/liquid separation.

Following this after-treatment, which may or may not be necessary, the filtrate contains the end products of the process, any unreacted liquid starting materials and the liquid amine bases together possibly with small quantities of water. Such water may optionally be removed by azeotropic distillation with one of the other solvent constituents. Further separation of the urethane-containing phase depends upon the nature of the solvent and of the excess organic compound containing hydroxy groups as well as the nature of the amine bases and of the urethane. Separation may be carried out in known manner by distillation and/or extraction and/or crystallization. The amine bases separated off may be recycled and, together with the recycled catalyst sludge or any fresh catalyst added, form the catalyst system for the next reaction mixture to be reacted in accordance with the process of the present invention. The other liquid streams accumulating in the working up stage, which contain for example water and excess hydroxy compounds and/or inert solvent and any unreacted nitro compound may also be returned to the reaction stage. The water-containing streams which are to be recycled may be freed from water before being reused by suitable methods (for example, by azeotropic distillation) to such an extent that the total water content of the liquid phases at the entrance to the reactor amounts to between about 0.1 and 0.8 wt. % and preferably to between 0.1 and 0.3 wt. %.

The products of the process of the present invention (urethanes) are suitable for use as pesticides and as intermediate products for the production of pesticides. However, the product urethanes are primarily of interest as starting materials for the production of the isocyanates on which they are based. This production of the isocyanates may be carried out in accordance with methods well known in the art. One such method is thermal splitting of the products obtained by the process of the present invention.

The invention is further illustrated, but is not intended to be limited by the following examples.

EXAMPLES 1 to 11

General Procedure:

The tests described in Examples 1–11 were carried out in a 0.7 liter stainless steel autoclave with, in each case, 200 g of ethanol and the other constituents of the starting mixtures characterized by % by weight. The filled autoclave was first purged with nitrogen and then charged at room temperature with the carbon dioxide (if used), carbon monoxide and hydrogen gases (in that order) to the partial pressures indicated. The mixture was heated with stirring to the reaction temperature. After the reaction, the reaction mixture was left to cool to room temperature. The gas phase was expanded through a gas meter into a gas bag from which a gas sample was removed for analysis by gas chromatography. The reaction mixture obtained was weighed out and analyzed by gas chromatography and also by high pressure liquid chromatography.

The selectivity is expressed in mole percent, based on the nitrobenzene reacted. If the starting mixture contained amines which could also occur as reaction products, the quantities of amine starting material used are subtracted beforehand from those observed for the calculation of selectivity. A selectivity $S_I$ is quoted for phenyl urethane, corresponding to the phenyl urethane directly obtained from nitrobenzene. Another selectivity for phenyl urethane, $S_{II}$, is calculated from the sum of the selectivities of aniline, N-ethyl aniline, N,N'-diphenyl urea and $S_I$ and represents the overall selectivity obtainable for phenyl urethane where the secondary products are recycled.

The degree of hydrocarbonylation (HCD) is expressed in % and corresponds to 100 times the value x defined in equation (3). The HCD represents the percentage of urethane formed in accordance with equation (2), based on the total quantity of phenyl urethane formed. The HCD-value is calculated from the quantity of water formed. The quantities of water formed in the hydrogenation reactions and condensation reactions in accordance with equations (4) to (8) are determined in accordance with those equations and set aside in determining the HCD. A control value for the HCD may be determined from the $CO_2$-analysis of the expanded reaction gas. However, since $CO_2$ also remains dissolved in the liquid reaction products and is not analytically determined, this method always gives a slightly high value for the HCD.

EXAMPLE 1

A mixture of 73.2 wt. % ethanol, 18.3 wt. % nitrobenzene, 3.7 wt. % aniline, 2.9 wt. % $\alpha$-$Fe_2O_3$, 1.8 wt. % $VOCl_3$ and 80 ppm of $PdCl_2$ was reacted for 1 hour at 180° C. with 60 bars CO and 60 bars hydrogen. The nitrobenzene conversion amounted to 84% and the product selectivities were 0.5 mol % for aniline, 7.0 mol % for N-ethyl aniline, 0.6 mol % for N,N-diethyl aniline, 1.9 mol % for quinaldine, 8.7 mol % for N,N'-diphenyl urea and $S_I$=81.3 mol % and $S_{II}$=97.5 mol % for phenyl urethane. The HCD-value was 62%.

EXAMPLE 2

A mixture of 75.15 wt. % ethanol, 18.8 wt. % nitrobenzene, 3.8 wt. % aniline, 0.75 wt. % CuO, 0.75 wt. % $CuCl_2$, 0.75 wt. % pyridine hydrochloride and 80 ppm of $PdCl_2$ was reacted for 2 hours at 180° C. with 60 bars CO and 60 bars hydrogen. The nitrobenzene conversion amounted to 83% and the product selectivities were 19.4 mol % for N-ethyl aniline, 10.9 mole % for N-ethyl aniline, 2.4 mole % for quinaldine, 11.1 mole % for N,N'-diphenyl urea and $S_I$=54.7 mole % and $S_{II}$=96.1 mole % for phenyl urethane. The HCD-value amounted to 74%.

EXAMPLE 3

A mixture of 66.2 wt. % ethanol, 26.1 wt. % nitrobenzene, 1.6 wt. % aniline, 0.3 wt. % N-ethyl aniline, 0.9 wt. % quinaldine, 0.3 wt. % N,N'-diphenyl urea, 0.3 wt. % $MnCl_2$, 1.0 wt. % $FeCl_2.2H_2O$, 3.3 wt. % $\alpha$-$Fe_2O_3$ and 296 ppm of $PdCl_2$ was reacted for 2 hours at 180° C. with 80 bars CO and 40 bars $H_2$. The nitrobenzene conversion amounted to 100% and the product selectivities were 4.8 mole % for aniline, 0.1 mole % for N-ethylaniline, 2.3 mole % for N,N'-diphenyl urea and $S_I$=92.0 mole % and $S_{II}$=99.2 mole % for phenyl urethane. The HCD-value was 61%.

EXAMPLE 4

A mixture of 65.7 wt. % ethanol, 16.0 wt. % nitrobenzene, 6.4 wt. % aniline, 3.2 wt. % N,N-diethylaniline, 6.6 wt. % $\alpha$-$Fe_2O_3$, 2.0 wt. % $FeCl_2.2 H_2O$ and 100 ppm of ruthenium chloride were reacted for 2 hours at 180° C. with 60 bars CO and 60 bars hydrogen. The nitrobenzene conversion amounted to 51% and the product selectivities were 17.0 mole % for aniline, 9.5 mol % for N-ethylaniline, 2.4 mol % for quinaldine, 10.0 mole % for N,N'-diphenyl urea and $S_I$=58.6 mole % and $S_{II}$=95.1 mole % for phenyl urethane. The HCD-value was 51%.

EXAMPLE 5

A mixture of 70.6 wt. % ethanol, 16.0 wt. % nitrobenzene, 3.2 wt. % aniline, 1.6 wt. % N,N-diethyl aniline, 6.6 wt. % $\alpha$-$Fe_2O_3$, 2.0 wt. % $FeCl_2.2H_2O$ and 100 ppm of palladium chloride were reacted for 1 hour at 180° C. with 60 bars CO and 60 bars hydrogen. The nitrobenzene conversion amounted to 99.4% and the product selectivities were 12.0 mole % for aniline, 5.0 mole % for N-ethyl aniline, 1.8 mole % for quinaldine, 2.4 mole % for N,N'-diphenyl urea and $S_I$=75.6 mole % and $S_{II}$=95.0 mole % for phenyl urethane. The HCD-value was 43%.

EXAMPLE 6

A mixture of 65.7 wt. % ethanol, 16.0 wt. % nitrobenzene, 6.4 wt. % aniline, 3.2 wt. % N,N-diethyl aniline, 6.6 wt. % $\alpha$-$Fe_2O_3$, 2.0 wt. % $FeCl_2.2H_2O$ and 100 ppm of $PdCl_2$ were reacted for 1 hour at 180° C. with 60 bars CO and 60 bars hydrogen. The nitrobenzene conversion amounted to 99.2% and the product selectivities were 0 mole % for aniline, 3.9 mole % for N-ethyl aniline, 0.5 mole % for quinaldine, 2.8 mole % for N,N'-diphenyl urea and $S_I$=92.6 mole % and $S_{II}$=99.3 mole % for phenyl urethane. The HCD-value was 52%.

EXAMPLE 7

A mixture of 67.2 wt. % ethanol, 26.5 wt. % nitrobenzene, 1.6 wt. % aniline, 0.3 wt. % $MnCl_2$, 3.4 wt. % $\alpha$-$Fe_2O_3$, 1.0 wt. % $FeCl_2.2H_2O$ and 300 ppm of $PdCl_2$ was reacted for 1 hour at 180° C. with 80 bars CO and 40 bars $H_2$. The nitrobenzene conversion amounted to 72% and the product selectivities were 0 mole % for aniline, 1.1 mole % for N-ethyl aniline, 0.3 mole % for quinaldine, 0.2 mole % for N,N'-diphenyl urea and $S_I=98.0$ mole % and $S_{II}=99.3$ mole % for phenyl urethane. The HCD-value was 64%.

This example shows that a high HCD-value can be obtained even with low nitrogen partial pressure in the reaction gas and with a $CO:H_2$-ratio of 2:1. Applied to continuous operation of the reaction using a gas recycling system, this result may be interpreted to mean that, although the $CO:H_2$-ratio in the starting gas should correspond as far as possible to the $CO:H_2$-ratio which is calculated as the $CO/H_2$-consumption in accordance with equation (3), the $CO/H_2$-ratio in the reaction gas or in the recycle gas should be adapted to meet the requirements of the reaction kinetics, i.e., the required HCD-value.

EXAMPLE 8

A mixture of 73.0 wt. % ethanol, 16.6 wt. % nitrobenzene, 3.3 wt. % aniline, 1.7 wt. % N,N-diethyl aniline, 3.3 wt. % $\alpha$-$Fe_2O_3$, 2.1 wt. % $FeCl_2.2H_2O$ and 100 ppm of $PdCl_2$ was reacted for 1 hour at 180° C. with 40 bars Co and 80 bars hydrogen in the presence of 40 bars $CO_2$. The nitrobenzene conversion amounted to 99.5% and the product selectivities were 55.0 mole % for aniline, 3.7 mole % for N-ethyl aniline, 0.4 mole % for quinaldine, 2.4 mole % for N,N'-diphenyl urea and $S_I=39$ mole % and $S_{II}=99.6$ mole % for phenyl urethane. The HCD-value was 32%.

EXAMPLE 9

A mixture of 69.2 wt. % ethanol, 15.7 wt. % nitrobenzene, 3.1 wt. % aniline, 1.6 wt. % N,N-diethyl aniline, 6.5 wt. % $\alpha$-$Fe_2O_3$, 3.9 wt. % $FeCl_2.2H_2O$ and 100 ppm of $PdCl_2$ was reacted for 1 hour at 180° C. with 40 bars CO and 80 bars hydrogen in the presence of 40 bars $CO_2$. The nitrobenzene conversion amounted to 99.9% and the product selectivities were 27.1 mole % for aniline, 4.0 mole % for N-ethyl aniline, 2.9 mole % for N,N'-diphenyl urea and $S_I=65.4$ mole % and $S_{II}=99.4$ mole % for phenyl urethane. The HCD-value was 61%.

By comparison with Example 8, this Example shows that any increase in the concentration of the iron-containing co-catalyst components suppresses the hydrogenation products in favor of the hydrocarbonylation reaction, even for a high hydrogen partial pressure.

EXAMPLE 10 (Comparison Example)

A mixture of 83.3 wt. % ethanol, 10.2 wt. % nitrobenzene, 1.6 wt. % aniline, 1.5 wt. % 1,4-diaza2,2,2-bicyclooctane and 0.4 wt. % metallic selenium was reacted for 1 hour at 180° C. with 60 bars CO and 60 bars hydrogen. The nitrobenzene conversion amounted to 86% and the product selectivities were 0.2 mole % for quinaldine, 5.4 mole % for N,N'-diphenyl urea and $S_I=89.7$ mole % and 95.1 mole % for phenyl urethane. The HCD-value was 1.9%.

EXAMPLE 11 (Comparison Example)

The procedure was the same as in Example 10, except that 600 ppm of palladium chloride were included. The nitrobenzene conversion amounted to 99.5% and the product selectivities were 0.4 mol % for quinaldine, 4.4 mole % for N,N'-diphenyl urea and $S_I=92.8$ mole % and $S_{II}=97.2$ mole % for phenyl urethane. The HCD-value was 0%.

Comparison Examples 10 and 11 show that although high urethane yields may be obtained using catalyst systems containing Se or Se and Pd, even with $CO/H_2$-mixtures, a reaction according to equation (2) takes place to a very limited extent only, if at all. This fact is evidenced by the HCD-value obtained in these comparative examples. In other words, the urethane-forming reaction takes place with hardly any consumption of hydrogen.

EXAMPLE 12

In a 0.7 liter stainless steel autoclave, 60 bars CO and 60 bars hydrogen were added to a mixture of 200 g of ethanol, 20 g of 2,4-dinitrotoluene, 5 g of pyridine, 4 g of 2,4-diaminotoluene, 15 g of $\alpha$-$Fe_2O_3$, 5 g of $FeCl_2.2H_2O$ and 25 mg of palladium chloride, followed by reaction for 1 hour at 180° C. After cooling, the autoclave was opened, 10 g of 2,4-dinitrotoluene were added to the contents of the autoclave and the reaction was again carried out in the same way with fresh $CO/H_2$-mixture. Analysis of the product by high pressure liquid chromatography showed a 100% conversion of the 2,4-dinitrotoluene. The selectivities were 14.5 mole % for monourethanes and 43 mole % for toluene-2,4-dicarbamate, the required bisurethane. In addition, urea-like products were detected. The HCD-value was calculated at 45%. The secondary products were recyclable and gave the required bisurethane.

EXAMPLES 13 to 16

General Procedure:

To carry out the tests on a continuous basis, a reactor cascade was made from two 2.5 liter stirrer-equipped vessels (Hastelloy C) each with a filling level of 2.2 liters connected by a tube. The first vessel was supplied with a constant gas stream of CO and $H_2$ by means of a throughflow governor and with the suspension which contained all the non-gaseous starting materials from a vigorously stirred reservoir via a piston pump. If $CO_2$ was also used, it was separately delivered in liquid form, evaporated in a heated feed pipe and added to the remaining gas stream before the gas stream was fed to the reactor. The reactors were electrically heated and stirred by means of a magnetic coupling. The reaction pressure was maintained at the exit of the second reactor with a regulating valve through which the entire reaction mixture was vented. All suspension-carrying pipes in the pressure section and after the regulating valve were heated to approximately 100° C. The products were separated in a glass separator into a suspension and a gas phase and the individual phases were balanced and analyzed. The method used for analysis and evaluation was the same as that used for Examples 1–11. Each of the tests lasted 24 hours, the test results being average values from 3 analyses in each case. i.e., from samples taken at 8-hour intervals.

EXAMPLE 13

The starting materials were 70.6 wt. % ethanol, 16.0 wt. % nitrobenzene, 3.2 wt. % aniline, 1.6 wt. % N,N-diethylaniline, 6.6 wt. % $\alpha$-$Fe_2O$, 2.0 wt. % $FeCl_2.2H_2O$ and 110 ppm of $PdCl_2$.

| | | |
|---|---|---|
| Throughput of the suspension: | 2000 g/h | gas composition |
| CO-throughput: | 588 g/h | at the reactor |
| $H_2$-throughput | 42 g/h | entrance: 50% |
| Reaction pressure: | 90 bars | by volume of |
| Reaction temperature: | 180° C. | CO, 50% by volume of $H_2$ |

The nitrobenzene conversion amounted to 100% and the selectivity for the recyclable secondary products was 17 mole %, $S_I=79$ mole % and $S_{II}=96$ mole % for phenyl urethane. The HCD-value was 68%.

EXAMPLE 14

The procedure was the same as in Example 13, except that 1320 g/h of $CO_2$ were additionally introduced, producing a gas composition at the reactor entrance of 42% by volume of $CO_2$, 29% by volume of CO and 29% by volume of $H_2$.

The nitrobenzene conversion amounted to between 97% and 100% and the selectivity for the recyclable products was 19 mole %, $S_I=75$ mole % and $S_{II}=94$ mole % for phenyl urethane. The HCD-value was 61%.

EXAMPLE 15

The starting materials were 77.3 wt. % ethanol, 16.0 wt. % nitrobenzene, 1.6 wt. % aniline, 0.8 wt. % N,N-diethylaniline, 3.3 wt. % $\alpha$-$Fe_2O_3$, 1.0 wt. % $FeCl_2.2$-$H_2O$ and 110 ppm of $PdCl_2$.

| Throughput of the suspension: | 2000 g/h | gas composition |
| --- | --- | --- |
| CO-throughput | 588 g/h | at the reactor |
| $H_2$-throughput | 60 g/h | entrance: |
| $CO_2$-throughput | 924 g/h | 29% by volume |
| Reaction pressure: | 90 bars | of CO, 42% by |
| Reaction temperature: | 180° C. | volume of $H_2$ |
| | | and 29% by |
| | | volume of $CO_2$ |

The nitrobenzene conversion amounted to 90% and the selectivity for the recyclable secondary products was 42 mole %, $S_I=55$ mole % and $S_{II}=97$ mole % for phenyl urethane. The HCD-value was 51%.

EXAMPLE 16

The procedure was the same as in Example 15, except that 4 times the quantity of aniline and N,N-diethyl aniline was used in the starting mixture.

The nitrobenzene conversion amounted to 92% and the selectivity for the recyclable secondary products was 22 mole %, $S_I=75$ mole % and $S_{II}=97$ mole % for phenyl urethane. The HCD-value was 76%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a urethane in which an organic nitro compound is reacted with an organic compound containing at least one hydroxyl group in the presence of carbon monoxide, hydrogen and a catalyst system which catalyst system comprises
   (1) at least one noble metal or compound of a noble metal in Group VIIIB of the Periodic System of Elements,
   (2) at least one co-catalyst which is a combination of
      (a) at least one oxidic or hydroxidic compound of iron or copper and
      (b) at least one compound containing chlorine anionically bound as chloride selected from
         (i) chlorides and oxychlorides of elements of Groups IIIA, IVA, VA, and/or I-VIII B of the Periodic System of Elements other than the noble metals of Group VIII B and/or
         (ii) organic ammonium chlorides and
   (3) at least one organic nitrogen base in which the carbon monoxide and hydrogen are used in quantities such that the molar ratio of carbon monoxide to hydrogen is from 0.3:1 to 3:1.

2. The process of claim 1 in which noble metal component (a) of the catalyst system is selected from palladium in finely divided metallic form, ruthenium in finely divided metallic form, soluble compounds of palladium, soluble compounds of ruthenium and combinations thereof.

3. The process of claim 2 in which catalyst component (2)(a) is an oxide and/or oxide hydrate of trivalent iron.

4. The process of claim 3 in which catalyst component (b 2)(b) is selected from iron(II)chloride, iron (III) chloride, hydrates of iron(II)chloride, hydrates if iron (III)chloride, amine complexes of iron (II)chloride, amine complexes of iron(III)chloride and mixtures thereof.

5. The process of claim 4 in which the organic nitrogen base (3) is a primary or secondary amine which is structurally related to the organic nitro compound and/or organic hydroxyl compound used as a starting material.

6. The process of claim 2 in which the catalyst component (2)(b) is selected from iron (III) chloride, iron-(III)chloride, hydrates of iron(II) chloride, hydrates of iron(III)chloride, amine complexes of iron(II)chloride, amine complexes of iron (III) chloride and mixtures thereof.

7. The process of claim 1 in which the catalyst component (2)(b) is selected from iron(II) chloride, iron-(III)chloride, hydrates of iron(II) chloride, hydrates of iron(III)chloride, amine complexes of iron(II)chloride, amine complexes of iron (III)chloride and mixtures thereof.

8. The process of claim 1 in which the catalyst component (b 2)(a) is an oxide and/or oxide hydrate of trivalent iron.

9. The process of claim 1 in which the organic nitrogen base (3) is a primary or secondary amine which is structurally related to the organic nitro compound and/or organic hydroxyl compound used as a starting material.

10. The process of claim 1 in which the reaction is carried out continuously in a cascade of reactors.

11. The process of claim 10 in which a gas mixture leaving the last reaction vessel is recycled.

12. The process of claim 11 in which the gas mixture to be recycled is treated in a manner such that 20 to 60 volume percent of the gas mixture is carbon dioxide.

13. The process of claim 1 in which the urethane-containing product mixture is separated from the catalyst by crossflow-filtration.

14. The process of claim 13 in which the catalyst is reused.

15. The process of claim 13 in which the product urethane is recovered from the urethane-containing mixture by distillation and/or extraction and/or crystallization.

* * * * *